US006435870B1

(12) United States Patent
Walde

(10) Patent No.: US 6,435,870 B1
(45) Date of Patent: Aug. 20, 2002

(54) ORTHODONTIC DISTALIZING APPLIANCE

(76) Inventor: Kevin C. Walde, #6 Lancaster Ct., Washington, MO (US) 63090

( * ) Notice: Subject to any disclaimer, the term of this patent is extended or adjusted under 35 U.S.C. 154(b) by 0 days.

(21) Appl. No.: 09/672,921

(22) Filed: Sep. 28, 2000

(51) Int. Cl.7 ................................................ A61C 3/00
(52) U.S. Cl. ................................ 433/7; 433/18; 433/24
(58) Field of Search ............................ 433/6, 7, 18, 24

(56) References Cited

U.S. PATENT DOCUMENTS

| 3,293,747 A | 12/1966 | Denholtz | 32/14 |
| 4,202,100 A | 5/1980 | Förster | 433/7 |
| 4,571,178 A | 2/1986 | Rosenberg | 433/18 |
| 4,713,000 A | 12/1987 | Rosenberg | 433/18 |
| 4,723,910 A | 2/1988 | Keller | 433/7 |
| 5,002,485 A | * 3/1991 | Aagesen | 433/7 |
| 5,022,855 A | 6/1991 | Jeckel | 433/18 |
| 5,064,370 A | 11/1991 | Jones | 433/21 |
| 5,622,493 A | 4/1997 | Razdolsky et al. | 433/7 |
| 5,645,422 A | 7/1997 | Williams | 433/7 |
| 5,769,630 A | * 6/1998 | Hoffman | 433/18 X |
| 5,785,520 A | * 7/1998 | Carano et al. | 433/18 X |
| 5,829,970 A | 11/1998 | Yousefian | 433/7 |
| 5,873,715 A | 2/1999 | Liou | 433/18 |
| 5,885,290 A | 3/1999 | Guerrero et al. | 606/71 |
| 5,904,479 A | 5/1999 | Staples | 433/7 |
| 5,967,772 A | * 10/1999 | Gray | 433/18 X |
| 6,109,916 A | * 8/2000 | Wilcko et al. | 433/7 X |

OTHER PUBLICATIONS

Journal of Clinical Orthodontics—Nov. 1992—The Pendulum Appliance for Class II Non–Compliance Therapy—pp. 706–714—James J. Hilders.
The Angle Orthodontist—vol. 67, No. 4, 1997—Distal Molar Movement Using Pendulum Appliance pp. 261–270—Freidrich K. Byloff et al.
Straumann Dental Booklet—Jun. 1997—Orthosystems–Ortho Info.
The Use of Palatal Implants for Orthodontic Anchorage—Clinical Oral Implants Research—1996:7—pp. 410–416—H. Wehrbein et al.
The Modified Pendulum Appliance with Removable Arms—JCO—Apr. 2000—pp. 244–246 Giuseppe Scuzzo et al.
Journal of Orofacial Orthopedics—Sonderdruck 57 (1996), Nr. 3, 142–153—H. Wehrbein et al.
Straumann Dental—Mar. 1999—Ortho Implant and Bonding Base.
Journal of Clinical Orthodontics—Jul. 2000—pp. 397–402—Absolute Anchorage in Orthodontics: Direct and Indirect Implant–Assisted Modalities—Frank Celenza et al.
Journal of Clinical Orthodontics—Jul. 2000—pp. 419–423—Molar Distalization with a Modified Distal Jet Appliance—Andrew N. Quick et al.
Seminars in Orthodontics, vol. 4, No. 1—Mar. 1998—pp. 17–25—Hyperefficient Orthodontic Treatment Using Tandem Mechanics—James J. Hilgers.
American Orthodontics Leaflet—The Distal Jet—Undated—Aldo Carano.
Forestadent USA—Expansion Screws—pp. 6–2–6–13—Undated.

* cited by examiner

*Primary Examiner*—Nicholas D. Lucchesi
(74) *Attorney, Agent, or Firm*—Polster, Lieder, Woodruff & Lucchesi, L.C.

(57) ABSTRACT

This orthodontic distalizing appliance includes a forward support assembly having an anchoring base in the roof of the mouth. A rearward laterally disposed spring assembly is provided having outer ends removably received within associated sheaths attached to maxillary molars. A centrally disposed adjustment assembly extends between the anchoring base and the spring assembly for applying a force to the spring assembly which is transmitted to the molars to be distalized.

21 Claims, 5 Drawing Sheets

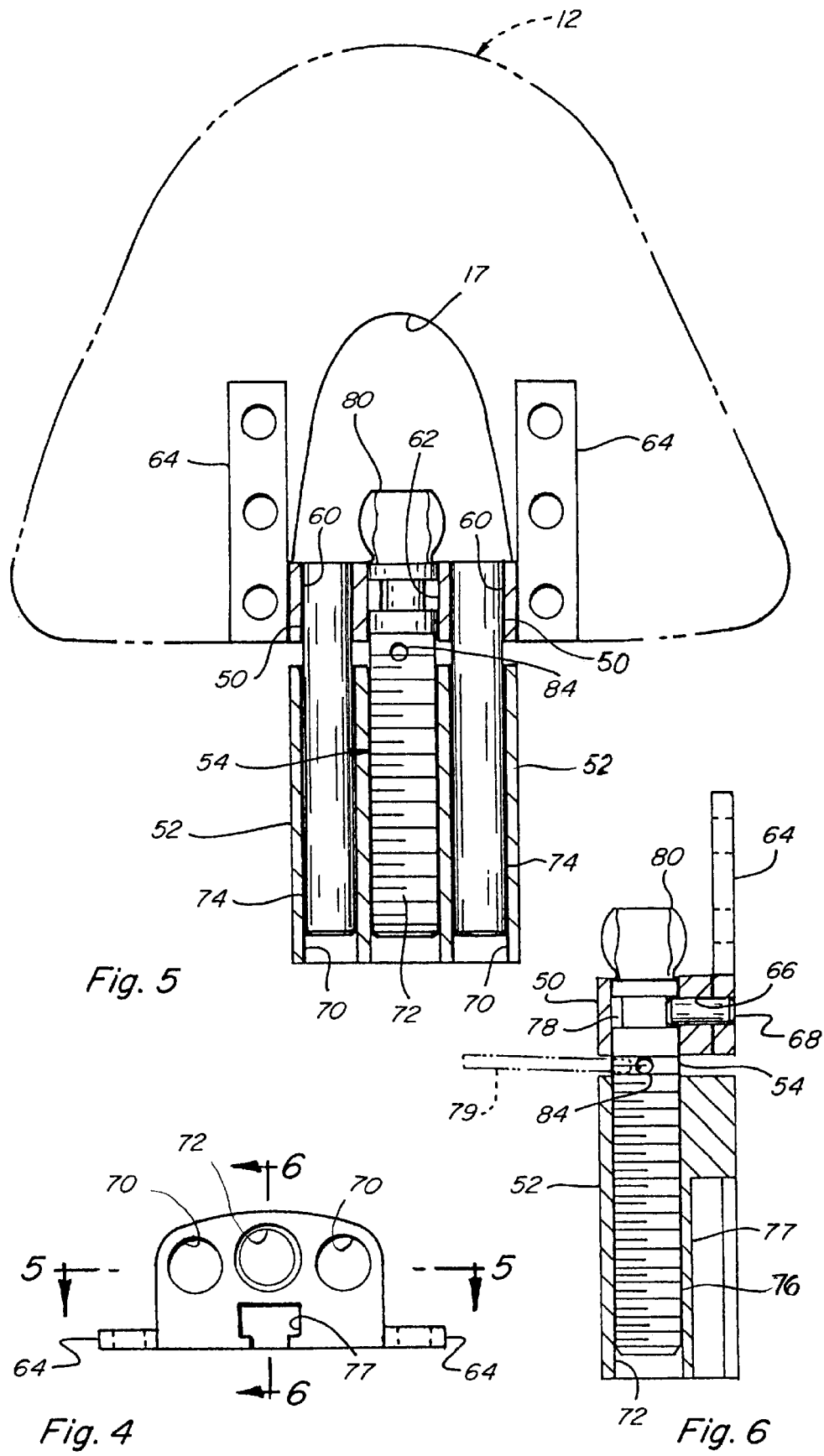

ORTHODONTIC DISTALIZING APPLIANCE

BACKGROUND OF THE INVENTION:

This invention relates generally to appliances for correcting malocclusion problems by non-extraction molar distalization methods and in particular to an appliance which uses a forward anchorage assembly, a rearward spring assembly and a threadedly adjustable device extending between the forward and rearward assemblies for achieving distalization.

One of the most well-known appliances used in modern orthodontics for correcting class II malocclusions is the Pendulum Appliance described by James J. Hilgers in the November 1992 issue of the Journal of Clinical Orthodontics in an article entitled The Pendulum Appliance for Class II Non-Compliance Therapy pp. 706–714, which is incorporated herein by reference. The Pendulum Appliance uses a large Nance acrylic button in the palatal area which is anchored by a wire attachment assembly to the upper premolars, in combination with a spring assembly which is attached between the mid-point of the button and the first upper molars to deliver a light continuous force to these molars without affecting the disposition of the Nance button. The spring assembly is connected at its outer ends to lingual sheaths attached to associated banded molars. Adjustment of the spring pressure is by manipulation of the spring assembly. Hilgers' appliance is an important improvement to the dental art but has limited adjustment capability.

An improved Pendulum Appliance is described in Vol. 67, No. 4 1997 of The Angle Orthodontist entitled Distal Molar Movement Using The Pendulum Appliance pp. 216–270, by Freidrich K. Byloff, et al. which is incorporated herein by reference. This pendulum appliance incorporates molar uprighting bends.

Another appliance is described in U.S. Pat. No. 5,785,520 which is incorporated herein by reference. This patent discloses an appliance using a Nance button having a framework which is anchored to opposed premolars. A pair of spring loaded adjustable pusher elements are interposed between the Nance button framework and lingual sheaths attached to banded molars rearwardly disposed of the Nance button. The telescopic pusher elements are arranged on the lingual side of the dental arch and may be lengthwise adjusted at each side of the arch to vary the force on a banded tooth. The appliance of U.S. Pat. No. 5,785,520 is considerably more complicated in its structural arrangement of parts than the Hilger's appliance and requires adjustment on both sides of the appliance.

None of the known prior art appliances incorporates a centrally located threaded adjustment feature for applying a variable force on the molars to which distalizing forces are applied.

SUMMARY OF THE INVENTION:

This orthodontic distalizing appliance uses a threadedly adjustable expansion device for applying distalizing pressure to molars on the lingual side of the dental arch.

The appliance provides advantages which are desirable in a successful distalizing device namely the utilization of an anchoring base such as a Nance button or palatal implant to provide superior anchorage of the appliance; predictable results with a minimum of undesirable side effects; easy accessibility to the adjustment device and ready replacement of the force-applying spring assembly and an overall reduction in patient chair time.

This invention provides an orthodontic distalizing appliance comprising a forward support assembly including an anchoring base adapted to seat in the upper part of the mouth. A rearward spring assembly is provided including spring means having a first portion and at least one outwardly extending second portion, said second portion being removably attached to a tooth. An adjustment means is provided including a forward portion fixedly attached to the base and a rearward portion receiving the spring means in removable relation together with means connecting the first and second portions together in movable relation for applying a force to the second portion of the spring means and the tooth to which it is attached.

It is an aspect of the invention to provide that the adjustment means includes a screw having a first portion attached in freely rotatable relation to the forward portion, said screw having a second portion threadedly connected to the rearward portion so that the rearward portion is movable relative to the forward portion when the screw is rotated.

It is another aspect of the invention to provide that the adjustment means includes a pair of slide rods connecting said first and second portions together in sliding relation.

It is still another aspect of the invention to provide that the screw first portion includes a tool-acceptable portion by which the screw is rotatable to move the forward and rearward portions relative to each other.

It is yet another aspect of the invention to provide that the head of the screw is faceted and adapted to accept a tool in angular relation.

It is an aspect of the invention to provide that the forward portion of the adjustment means includes laterally disposed forwardly extending portions fixedly attached to the base.

It is another aspect of the invention to provide that the anchoring base is a Nance button formed from plastic material and the laterally disposed portions are embedded in said Nance button.

It is still another aspect of the invention to provide that the base includes outwardly extending portions embedded in the Nance button at an inner end and are adapted to be cemented to a tooth at an outer end.

It is yet another aspect of the invention to provide that the spring assembly includes opposed, tooth-attachable sleeves, and outer ends receivable into associated sleeves in removable relation.

It is an aspect of this invention to provide that the adjustment means rearward portion includes a slot, and the spring assembly includes a forwardly extending intermediate portion removably received by said slot.

It is another aspect of the invention to provide that the spring means includes a forwardly extending intermediate portion and outwardly extending portions each adapted to be removably attached to a tooth; and the adjustment means is centrally located and the rearward portion includes a slot receiving the intermediate portion of the spring means in removable relation.

It is an aspect of this invention to provide that the anchoring base is a palatal endosseous implant attached to the roof of the mouth.

It is yet another aspect of the invention that the an adjustment device is attached to the implant by a support means extending between the implant and the adjustment device and another aspect that the support means includes a generally U-shaped wire having a bight portion attached to the implant and rearwardly extending arms attached to the adjustment device.

It is an aspect of the device that the parts may be supplied in kit form to the orthodontic practitioner.

This orthodontic distalizing appliance is relatively inexpensive to manufacture, easy to use and efficient in performing its intended purpose.

BRIEF DESCRIPTION OF THE DRAWINGS:

FIG. 4 is an end view of the pressure adjustment device;

FIG. 5 is a longitudinal cross-sectional view taken on Line 5—5 of FIG. 4;

FIG. 6 is a longitudinal cross-sectional view taken on Line 6—6 of FIG. 4;

FIG. 9 is an exploded perspective view of the palatal implant; and

FIG. 10 is a fragmentary end view of the spring assembly.

Figure 1:
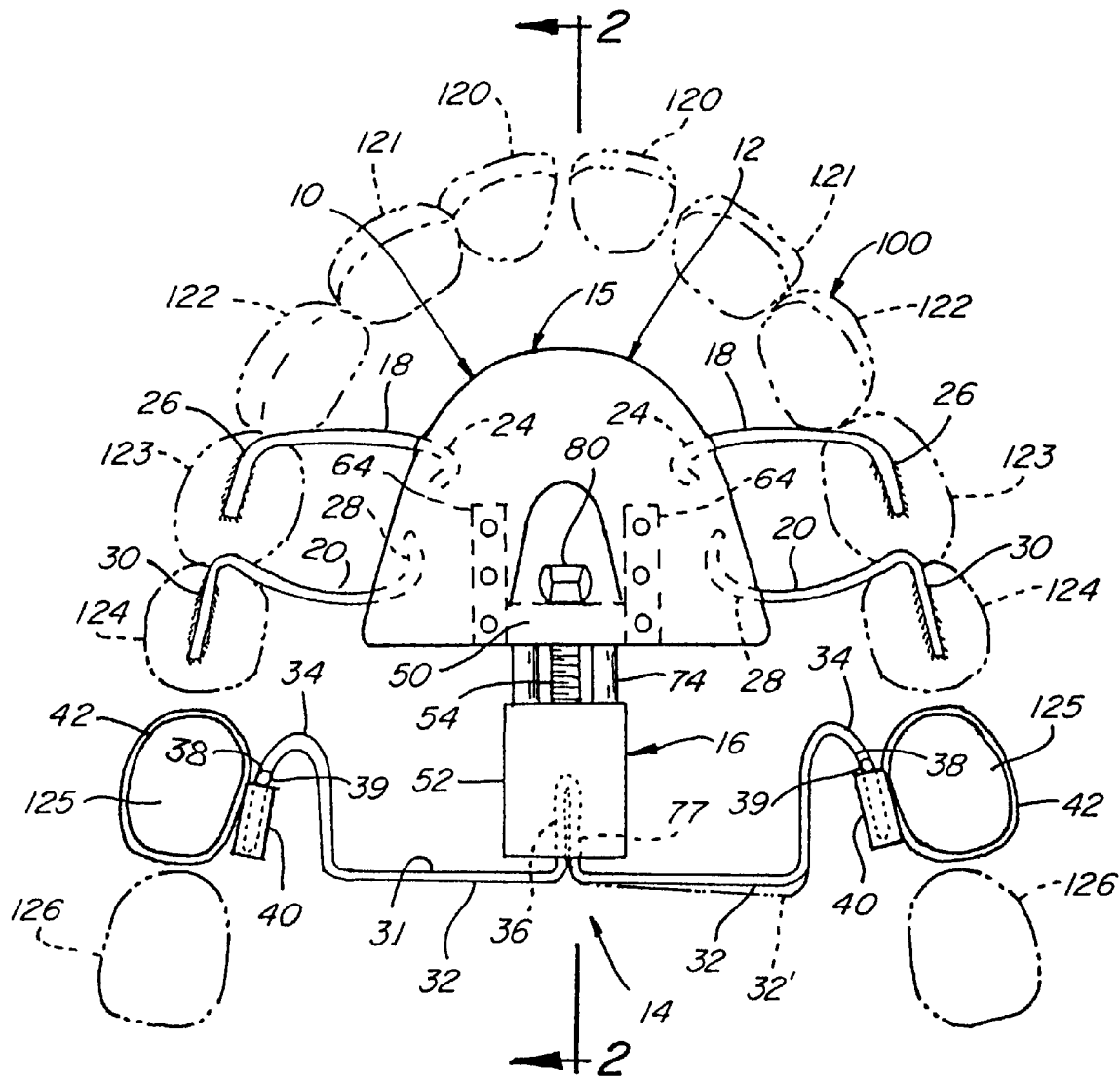
FIG. 1 is a plan view of the orthodontic distalizing appliance.
Figure 2:
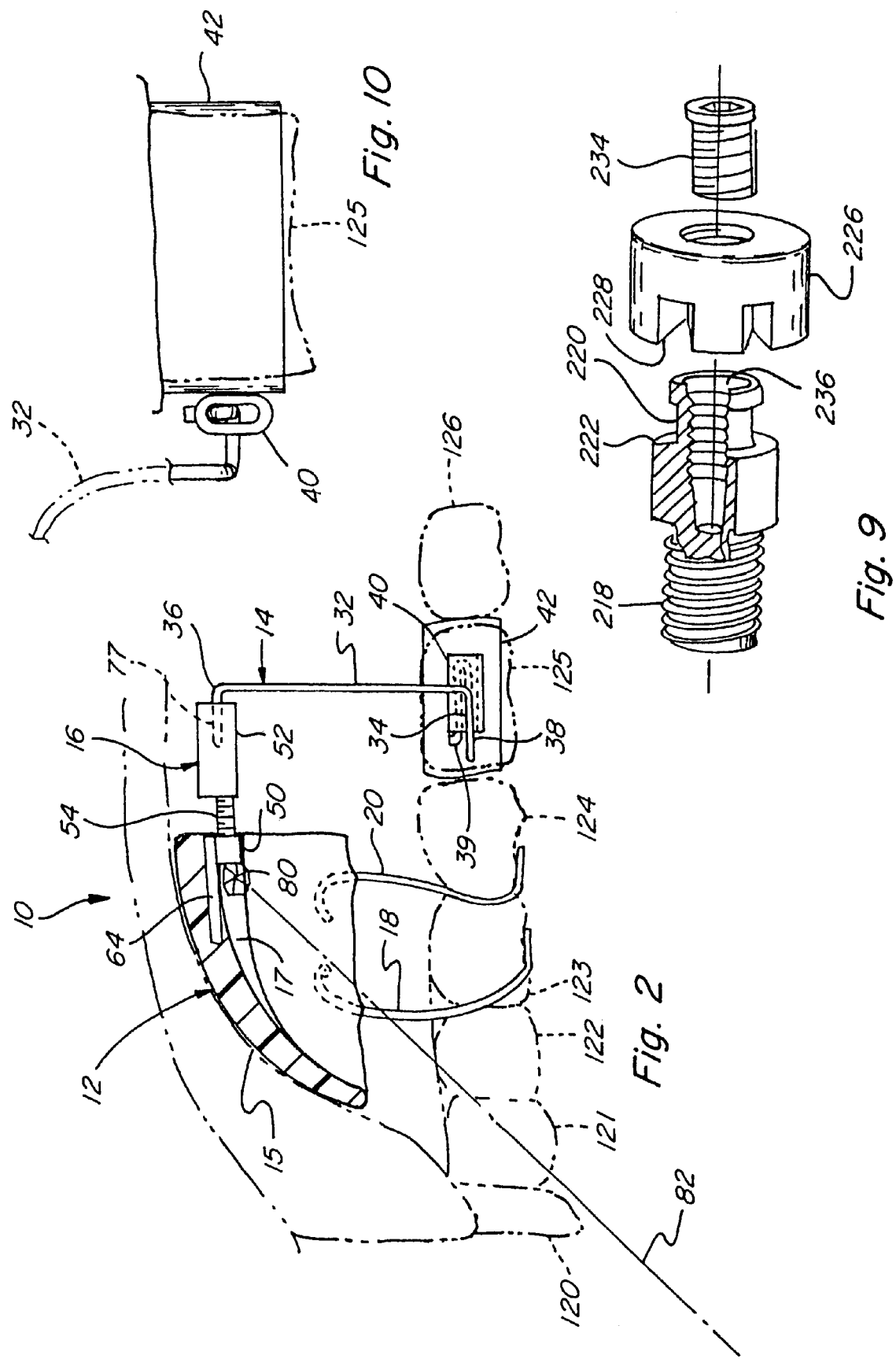
FIG. 2 is a cross-sectional view taken on Line 2—2 of FIG. 1.
Figure 3:
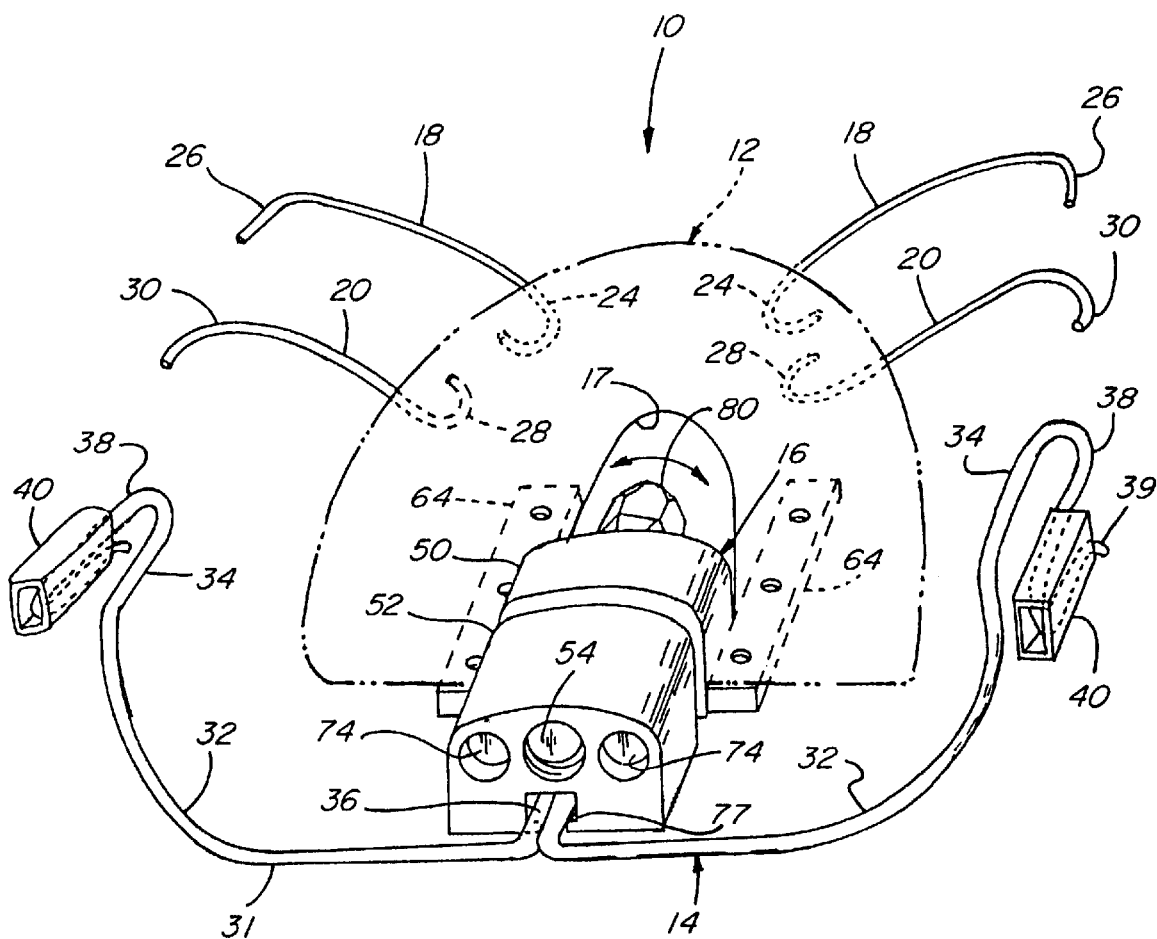
FIG. 3 is a perspective view of the pressure adjustment device.

DESCRIPTION OF THE PREFERRED EMBODIMENT:

Referring now by reference numerals to the drawings and first to FIGS. 1–3, it will be understood that the appliance 10 is intended for the purpose of distalizing molars by the application of a controlled pressure from a substantially fixed Nance button or other anchoring device such as an endosseous implant.

The appliance 10 is used in the area of the mouth generally known as the maxillary dental arch, more specifically the palate, indicated by numeral 100 and having a plurality of teeth arranged in an arch formation about the roof of the mouth and more particularly the palatal zone 102. The dental arch is further defined by the basal gingiva which provides a base for opposed sets of teeth consisting of the incisors 120 and 121, the canines 122, the premolars or bicuspids 123 and 124 and the molars 125 and 126.

The appliance 10 includes essentially a forwardly disposed support anchorage assembly 12, a spring assembly 14 and an adjustment device 16 which extends between a Nance button 15, providing part of the anchorage assembly 12, and the spring assembly 14.

The support assembly Nance button 15 is formed from plastic such as acrylic and arranged to fit into the palatal area. In addition to the Nance button 15, the support assembly 12 includes one or more pairs of arms 18 and 20 which may be formed, for example, from stainless steel wire by which the Nance button 15 is held in place. The anterior arms 18 include opposed inner ends 24 and outer ends 26. The inner ends 24 are molded into the plastic Nance button 12 and the outer ends 26 are connected onto premolars 123 as by cement. Similarly, the posterior arms 20 include opposed inner ends 28 and outer ends 30, the inner ends 28 are being molded into the plastic Nance button and the outer ends 30 being connected to premolars 124 as by cement. By this arrangement, the Nance button 15 is firmly held in place against the palate and provides a secure base for the adjustment device 16.

The spring assembly 14, best shown in FIGS. 1 and 3, is preferably formed from a single length of wire 31 and includes opposed loop portions 32, U-shaped outer end portions 34 and a U-shaped intermediate portion 36. In the embodiment shown, the loop portions 32, U-shaped portions 34 and intermediate portions 36 may be formed, for example, from a single length of 0.032" TMA® (Titanium Molybdenum Alloy) wire. As best shown in FIG. 1, the spring assembly 14 includes opposed sheaths or sleeves 40, which are welded or otherwise attached to banded molars 125. The sheaths 40 are arranged to removably receive the outer bayonet arms 38 of U-shaped portion 34 in sliding telescopic relation. The U-shaped intermediate portion 36 is arranged to be received in removable relation within an associated slot or passage provided in the expandable adjustment device 16 and indicated by numeral 77.

The adjustment device 16, which will now be described in detail, includes a forward body portion 50 fixedly attached to the Nance button 15 and a rearward body portion 52. The body portions 50 and 52 are movably connected by a screw 54 for relative axial movement of the rearward body portion 52 to apply pressure to the spring assembly 16 and exert a distalizing force against banded molars 125.

The parts of the adjustment device 16 are best understood by reference to FIGS. 4–6. As shown, the forward body portion 50, includes a pair of outer guide-receiving passages 60 and an unthreaded screw-receiving passage 62. The body portion 50 includes a pair of apertured outrigger arms 64, which are fixedly attached, as by welding, to the body portion 50 and are embedded into the Nance button 15 to secure the forward body portion 50 firmly to the anchoring means provided by the Nance button. The rearward body portion 52 also includes unthreaded guide-receiving passages 70 but a threaded screw-receiving passage 72. The passages 70 receive guides 74 in sliding relation and the threaded passage 72 receives the second, rearward threaded end 76 of the screw 54 in threaded relation.

As shown in FIG. 6, the forward portion 50 includes a threaded passage 66 receiving a set screw 68. At its first or forward end 75 the screw 54 includes an annular groove 78 which receives the set screw 68. This arrangement allows the screw 54 to rotate without axial movement. In the preferred embodiment, the screw 54 includes a hexagon faceted head 80 adapted to receive a socket wrench (not shown) so that the screw can be rotated by axial alignment with the screw head or by angled, non-axial alignment as shown by centerline 82 (FIG. 2) with the screw head 80. Alternatively, the head 80 may be provided with a socket adapted to receive an allen wrench (not shown).

The guides 74 are welded or otherwise secured to the forward body portion 50. The guides 74 are, however, free to slide in the passages of the rearward portion 52. This structural arrangement of parts provides that when the screw 54 is rotated, the rearward body portion 52 moves axially away from the forward body portion 50 and exerts a pressure against the spring intermediate portion 36 received within the slot 77 in rearward body portion 52. This pressure is transmitted to the outer bayonet ends 38 of the spring assembly 14 to exert a distalizing force against the sheaths 40, the bands 42, and the molars 125, to which they are attached.

It is thought that the structural arrangement of parts of this distalizing appliance 10 have become fully apparent from the foregoing description of parts, however, for completeness of disclosure, the installation and use of the appliance will be briefly described.

Initially, a cast is made of the patient's dental arch in a manner well-known to those skilled in the art. The Nance button 15 is formed from a piece of soft acrylic impressed on the cast palatal area. The preformed wires 18 and 20 can then be embedded into the soft acrylic plastic together with the outrigger arms 64. The forward portion 50 of the preassembled adjustment device 16 is embedded in the Nance button 15 when it is formed. It will be understood that the Nance button 15 is formed, in the embodiment shown, with a recess 17 so as to provide access for a socket wrench (not shown) into the area to be occupied by the faceted head 80 of the screw 54.

The spring assembly wire 31, includes portions 32, 34 and 36 and is prebent to suit the shape shown in FIG. 3 and the intermediate U-shaped portion 36 is inserted into the slot 77 of the rearward body portion 52. Using the plaster cast, (not shown), the support wires 18 and 20 embedded in the acrylic Nance button are cut to proper length to suit the premolars 123 and 124 to which they are to be cemented. Similarly, the bayonet portions 38 at the ends at the wire spring assembly 14 are bent to be received in the sheaths 40 which will be welded or soldered to the prefitted bands 42 of molars 125. As will be readily understood from FIG. 2, the bayonet portions 38 are reversely bent and include a turned up end 39 which engages the forward end of the sheath 40 and limits the extent to which the bayonet portions are received within the sheath, thereby transferring load from the spring assembly 14 to the sheath and hence the band 42 and molar 12.

Following this procedure and referring to FIG. 1, it is relatively simple matter to fit the Nance button 15, with the wires arms 18 and 20 attached and the adjustment device 16 attached, into the mouth of the patient, cement the arms 18 and 20 to associated premolars 123 and 124 and fit the spring assembly intermediate portion 36 into the receiving slot 77. The outer bayonet portions 38 can be fitted by pulling said portions forwardly and releasing them to slide into the associated sheaths 40. By rotating the screw 54, the desired pressure can be applied to the spring assembly 14. It will be understood that a different pressure can be applied to the left and right hand molars 125 by removing the spring assembly 14, and prebending one of the loop portions 32 to a different extent than the other loop 32 as shown in phantom outline by numeral 32'. Another option is to make the spring assembly with one side only or alternatively to provide a single or two individual adjustment devices 16, each associated with a banded molar 125. One of the advantageous features of the appliance 10 is the ease with which the wire portions of the spring assembly can be removed, adjusted and replaced.

As an alternative to using a faceted head 80 on the screw 54, which is rotatable by an elongate ball-jointed socket wrench or nut driver (not shown) which can be readily angled at 45°, it is possible to use an interfitting rod 79 in combination with a plurality of radially disposed predrilled sockets 84. The sockets 84 are disposed about the cylindrical surface of the screw 54 and the screw rotated by applying angular increments of movement to rod 79 indicated in FIG. 6.

Figure 7:
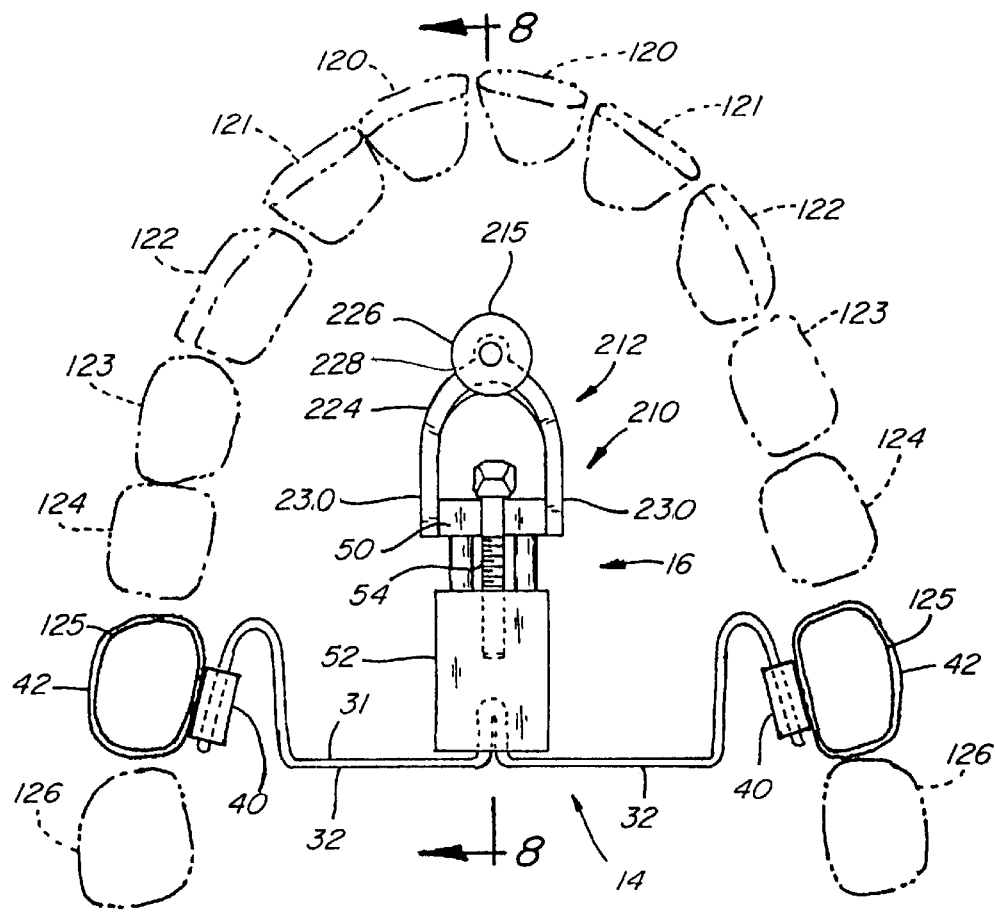
FIG. 7 is a plan view of a modified distalizing appliance utilizing a palatal implant in lieu of a Nance button.
Figure 8:
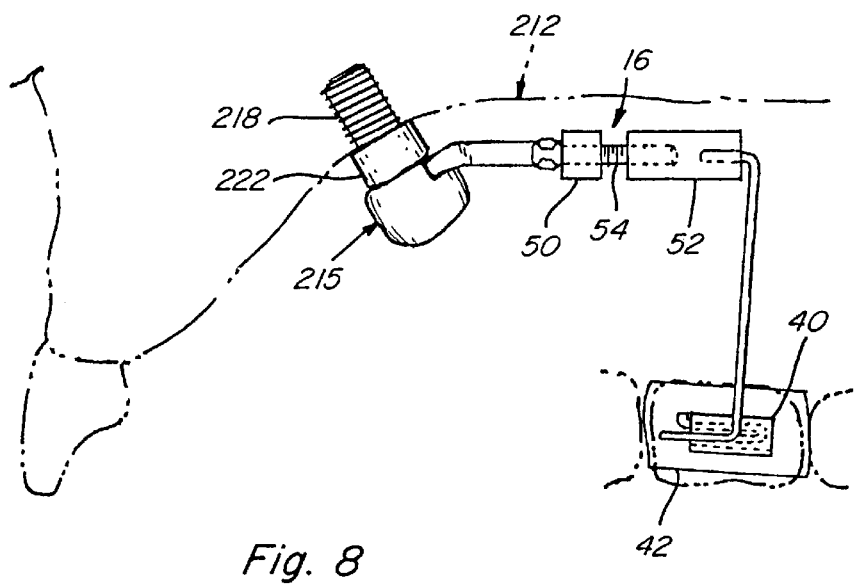
FIG. 8 is a cross-sectional view taken on Line 8—8 of FIG. 7.

Also, as suggested above, as an alternative to using a Nance button for an anchoring base, a dental implant known as an endosseous implant may be used. Implants of this type are disussed in Clinical Oral Implants Research 1996:7: in an article entitled The Use of Palatal Implants For Orthodontic Implants by H. Wehrbein et al. pp. 410–416. The modified distalizing appliance 210 is shown in FIGS. 7, 8 and 9. Endosseous implants of the type under consideration are available from Institut Straumann AG of Waldenburg, Switzerland and are illustrated in Orthosystems-Ortho Info a Straumann Dental Booklet dated June 1997 which is incorporated herein by reference.

Except for the substitution of an anchoring base provided by the endosseous implant and its support structure, the other components of the modified appliance 210 related to the spring assembly 14 and the adjustment device 16 are the same as described above. Accordingly, these parts will not be described in detail.

The anchoring base provided by the endosseous implant assembly 212 includes an implant 215 of titanium with a surface treated screw-shaped endosseous part 218 above the polished transmucosal neck 220. Below the neck there is an abutment 222 where transpalatal arches made from square section (0.032 in.×0.032 in.) U-shaped orthodontic wire 224 are held by means of an orthodontic clamping cap 226 which is provided with openings 228 receiving wire 224. The wire 224 is received by the neck 220, and arms 230 are welded or otherwise attached to the forward portion 50 of the adjustment device 14. The non-rotatable cap 226 includes a rotatable core portion provided by an occlusal screw 234 which is connected to the compatibly interiorly threaded portion 236 of the implant 215 by an allen wrench (not shown) to clamp the wires 224 between the cap 226 and the abutment 222.

In order to obtain good primary stability, the thread of the occlusal screw 215 is preferrably self-tapping. A more complete description of the endosseous implant and the implanting procedure may be found in the previously mentioned article found in Clinical Oral Implants Research 1996:7: pp. 410–416, which is incorporated herein by reference.

The distalizing appliances 10 and 210 described above may be supplied to the orthodontist in kit form. In the case of appliance 10, the kit consists of anchoring assembly parts, including stainless steel wire for anchoring arms 18 and 20; spring assembly parts including one or more lengths of TMA wire to form one or more springs 31 and one or more sheaths 40; and one or more adjustment devices 16 including a forward body portion 50, a rearward body portion 52, guides 74 and a screw 54. It will be understood that the adjustment devices may be supplied preassembled.

In the case of the modified distalizing device 210, the kit consists of the same components as described above except that the anchoring assembly is provided by an endosseous implant 215 and a length of wire for forming the U-shaped transpalatal arches 224.

Both kits will provide the necessary tools for installation and adjustment of the appliances.

Although the adjustable distalizing appliance has been described by making detailed reference to a preferred embodiment, such detail is to be understood in an instructive rather than in any restrictive sense, many variants being possible within the scope of the claims hereunto appended.

I claim as my invention:

1. An orthodontic distalizing appliance comprising:
   a forward support assembly including an anchoring base adapted to seat in the upper part of the mouth;
   a rearward spring assembly including spring means having a first portion and at least one outwardly extending second portion, said second portion being removably attached to a tooth; and
   adjustment means including a forward portion attached to the base and a rearward portion receiving the first portion of the spring means in removable relation and means connecting the forward and rearward portions together in movable relation for applying a force to the second portion of the spring means and the tooth to which it is attached.

2. A distalizing appliance as defined in claim 1, in which:

the adjustment means includes a screw having a first portion attached in freely rotatable relation to the forward portion, said screw having a second portion threadedly connected to the rearward portion so that the rearward portion is movable relative to the forward portion when the screw is rotated.

3. A distalizing appliance, as defined in claim 2, in which:

the adjustment means includes a pair of slide rods connecting said first and second portions together in sliding relation.

4. A distalizing appliance, as defined in claim 2, in which:

the screw first portion includes a tool-acceptable portion by which the screw is rotatable to move the forward and rearward portions relative to each other.

5. A distalizing appliance, as defined in claim 4, in which:

the head of the screw is faceted and adapted to accept a tool in angular relation from the anterior of the mouth.

6. A distalizing appliance, as defined in claim 1, in which:

the forward portion of the adjustment means includes laterally disposed forwardly extending portions fixedly attached to the base.

7. A distalizing appliance, as defined in claim 6, in which:

the anchoring base is a Nance button formed from plastic material and the laterally disposed portions are embedded in said Nance button.

8. A distalizing appliance, as defined in claim 1, in which:

the anchoring base is a Nance button formed from plastic material, and the base includes outwardly extending portions embedded in the Nance button at an inner end and are adapted to be cemented to a tooth at an outer end.

9. A distalizing appliance, as defined in claim 1, in which:

the spring assembly includes opposed, tooth-attachable sleeves, and outer ends receivable into associated sleeves in removable relation.

10. A distalizing appliance, as defined in claim 1, in which:

the adjustment means rearward portion includes a slot, and the spring assembly includes a forwardly extending intermediate portion removably received by said slot.

11. A distalizing appliance, as defined in claim 1, in which:

the spring means includes a forwardly extending intermediate portion and outwardly extending portions each adapted to be removably attached to a tooth; and the adjustment means is centrally located and the rearward portion includes a slot receiving the intermediate portion of the spring means in removable relation.

12. A distalizing appliance as defined in claim 1, in which:

the anchorage base is a palatal endosseous implant attached to the roof of the mouth.

13. A distalizing appliance as defined in claim 12, in which:

the adjustment device is attached to the implant by a support means extending between the implant and the adjustment device.

14. A distalizing appliance as defined in claim 13, in which:

the support means is a generally U-shaped wire having a bight portion attached to the implant and rearwardly extending arms attached to the adjustment device.

15. A kit for providing an orthodontic distalizing appliance comprising:

a forward support assembly including means for providing an anchoring base;

a rearward spring assembly including a spring;

an adjustment device including a forward portion attached to the anchoring base, a rearward portion receiving the spring in removable relation and a screw for threadedly connecting the forward and rearward portions together in movable relation.

16. A kit as defined in claim 15, in which:

the anchoring means includes means for providing a Nance button.

17. A kit as defined in claim 15, in which:

the anchoring means includes means for providing an endosseous implant.

18. An orthodontic distalizing appliance comprising:

a forward support assembly including an anchoring base adapted to seat in the upper part of the mouth;

a rearward spring assembly including spring means having a first intermediate portion and opposed outwardly extending second portions, said second portions being removably attached to an associated tooth; and adjustment means including a forward portion attached to the base and a rearward portion having a slot receiving the first portion of the spring means in removable relation and means connecting the forward and rearward portions together in movable relation for applying a force to the second portion of the spring means and the tooth to which it is attached.

19. A distalizing appliance as defined in claim 18, in which:

the spring means intermediate portion is generally U-shaped.

20. A distalizing appliance, as defined in claim 18, in which:

the forward portion of the adjustment means includes laterally disposed forwardly extending portions.

21. An orthodontic distalizing appliance comprising:

a forward support assembly including an anchoring base adapted to seat in the upper part of the mouth;

a rearward spring assembly including spring means having a first portion and at least one outwardly extending second portion, said second portion being removably attached to a tooth;

adjustment means including a forward portion attached to the base and a rearward portion receiving the first portion of the spring means in removable relation and means connecting the forward and rearward portions together in movable relation for applying a force to the second portion of the spring means and the tooth to which it is attached; and said means connecting the forward and rearward portions together including a screw connected between the forward and rearward portion so that the rearward portion is movable relative to the forward portion when the screw is rotated, said screw including a head adapted to accept a tool in angular relation from the anterior of the mouth.

* * * * *